(12) United States Patent
Goldberg (10) Patent No.: US 7,816,135 B2
(45) Date of Patent: Oct. 19, 2010

(54) METHOD OF ANALYZING LYMPHOCYTES

(75) Inventor: Edward Michael Goldberg, Redwood City, CA (US)

(73) Assignee: Becton, Dickinson and Company, Franklin Lakes, NY (US)

( * ) Notice: Subject to any disclaimer, the term of this patent is extended or adjusted under 35 U.S.C. 154(b) by 0 days.

(21) Appl. No.: 12/215,501

(22) Filed: Jun. 26, 2008

(65) Prior Publication Data

US 2009/0047690 A1 Feb. 19, 2009

Related U.S. Application Data

(60) Provisional application No. 60/958,382, filed on Jul. 5, 2007.

(51) Int. Cl.
*C12N 5/08* (2006.01)

(52) U.S. Cl. ..................................... 435/372; 435/374

(58) Field of Classification Search ........................ None
See application file for complete search history.

(56) References Cited

U.S. PATENT DOCUMENTS

| | | | |
|---|---|---|---|
| 6,905,874 B2 * | 6/2005 | Berenson et al. ............ | 435/375 |
| 2005/0221481 A1 * | 10/2005 | Migliaccio et al. .......... | 435/372 |
| 2009/0011456 A1 * | 1/2009 | Smith et al. ................. | 435/29 |

FOREIGN PATENT DOCUMENTS

| EP | 0 317 156 | 5/1989 |
|---|---|---|
| WO | WO 03001209 * | 3/2003 |
| WO | WO2006/056061 | 6/2006 |

OTHER PUBLICATIONS

Bohler, T. et al. "Evaluation of a Simplified Dual-Platform Flow Cytometric Method for Measurement of Lymphocyte Subsets and T-Cell Maturation Phenotypes in the Populations of Nouna, Burkina Faso," Clinical and Vaccine Immunology; vol. 14, No. 6: 775-781 (2007).
TriTEST CD3 FITC/CD4 PE/CD45 PerCP—50 Tests per Vial—calatog No. 340383; 50 Tests per Vial with TruCOUNT tubes—calatog No. 340402; Becton Dickinson. Apr. 2001 23-3027-03.
Wang-Rodriguez, J. et al. "Immune response to blood transfusión in very-low-birthweight infants," Transfusion, vol. 40: 25-34 (2000).

* cited by examiner

*Primary Examiner*—Michail A Belyavskyi
(74) *Attorney, Agent, or Firm*—Douglas A. Petry (57) ABSTRACT

The invention provides methods and compositions for identifying and counting lymphocytes in a biological sample, such as whole blood, by means of a probe comprising at least one binding compound specific for a T lymphocyte-specific marker, e.g. a CD2 or CD3, and at least one binding compound specific for CD45RA. Lymphocytes within the sample combine with such a probe to form a distinguishable subpopulation based on the amount of probe that specifically binds to their surfaces, thereby permitting such lymphocytes to be detected and enumerated on the basis of the intensity of the signal generated by the probe, and without the need of a separate physical measurement, such as light scatter. With additional probes specific for additional blood cell markers, percentages of lymphocytes, monocytes and granulocytes in a sample may be determined.

4 Claims, 3 Drawing Sheets

Fig. 3B under the page number (US 7,816,135 B2) is omitted.

METHOD OF ANALYZING LYMPHOCYTES

This application claims priority from U.S. provisional applications 60/958,382 filed Jul. 5, 2007, which is hereby incorporated by reference in its entirety.

BACKGROUND

Cell surface markers permit the identification of cellular phenotypes characteristic of both healthy and disease states, e.g. Maecker et al, J. Clin. Immunol., 20: 391-399 (2000); Rothe et al, Leukemia, 10: 877-895 (1996); Reilly et al, J. Clin. Pathol., 54: 508-511 (2001). Such markers are typically measured by staining a cell sample with a selection of labeled antibodies specific for different markers, followed by multi-parameter analysis by imaging or by flow cytometry, e.g. Stewart, Immunophenotyping (Wiley-Liss, 2000). Multi-parameter analysis using labeled antibodies, or immunophenotyping, has been particularly useful for identifying distinct functional and developmental classes of white blood cells, which has important applications in the classification of blood-related diseases, such as leukemias and lymphomas, and in the monitoring the status of HIV infected individuals. In the latter application, it is particularly desirable to measure absolute number per unit blood volume of T helper lymphocytes, as well as the relative number of such cells within total lymphocytes. These are challenging measurements by immunophenotyping because the characteristic cell surface markers of such cells are shared to varying degrees with non-lymphocyte white blood cells. Consequently, most current approaches for identifying lymphocyte populations require the measurement of at least one cellular property, such as forward or side light scatter when a flow system is employed, in addition to measurements based on cell surface markers.

It would be highly advantageous, particularly for low-cost point-of-care applications, if there were available methods and compositions for analyzing white blood cells, particularly lymphocytes, and their respective subsets solely on the basis of cell surface markers.

SUMMARY OF THE INVENTION

The invention provides methods and compositions for analyzing white blood cells. In one aspect, the invention is a method of identifying lymphocytes in a biological sample, especially a blood or lymphatic fluid sample, by using a probe comprising at least one binding compound specific for T-lymphocytes, e.g. a CD2- or CD3-specific antibody, and at least one binding compound specific for CD45RA molecules. Lymphocytes within a biological sample, such as a blood sample, combined with such a probe to form a distinguishable subpopulation based on the amount of probe that specifically binds to their surfaces, thereby permitting such lymphocytes to be detected and enumerated.

In another aspect, the invention provides a convenient method of measuring the percentage CD4+ lymphocytes (T-helper cells) in a population of lymphocytes without the need of size-based measurements, such as light scatter. Such aspect is implemented by using a probe as described above (first probe) in combination with a second probe comprising at least a third binding compound specific for CD4 molecules. When the second probe is labeled with a fluorescent dye distinct from that of the first probe, the CD4+ subpopulation is identified as a distinguishable cluster with high first-probe signal values in a two-dimensional plot of fluorescent signal intensities.

In another aspect, the invention provides a method of measuring a percentage of lymphocytes, monocytes, or granulocytes present in a sample of whole blood. In one embodiment, total white blood cells in a whole blood sample are approximated as the total of lymphocytes plus monocytes, plus granulocytes. In this aspect, the invention may be implemented by providing (i) a first probe as described above, (ii) a second probe comprising a binding compound specific for a monocyte-specific marker, such as CD14, wherein a portion of such binding compound is labeled with the same optical label as the first probe (a first optical label) and the remainder being labeled by a distinct optical label (a second optical label), and (iii) a third probe comprising a binding compound specific for a granulocyte-specific marker, such as CD15, wherein such binding compound is labeled with the second optical label. The first, second and third probes are mixed with a sample of whole blood under conditions that permit the respective binding compounds to specifically bind to their target antigenic determinants, after which the cells and their respective labels are identified, and counted, using conventional cell analysis techniques, such as a flow cytometer or microscope. When a population of white blood cells in a sample are analyzed in accordance with this aspect, lymphocytes are identified as cells having high signals from the first optical label and low signals from the second optical label; granulocytes are identified as cells having low signals from the first optical label and high signals from the second optical label; and monocytes are identified as cells having high signals from both the first and second optical labels. In an embodiment of this aspect, the binding compound specific for monocytes may be labeled with a third optical label distinct from the first and second optical labels.

In further embodiments, other lymphocyte subpopulations can be identified by using probes containing binding compounds specific for characteristic surface molecules.

The invention provides a convenient and effective method for identifying lymphocytes, for either absolute counts or percentage of white blood cell measurements, in a blood sample solely on the basis of surface markers, without the need of light scatter-based measurements to distinguish lymphocytes from other white blood cell types, such as monocytes or granulocytes.

The invention is particularly well-suited for use with image-based cell identification devices to provide measurements of percent CD4+ populations in whole blood samples.

DETAILED DESCRIPTION OF THE INVENTION

The practice of the present invention may employ, unless otherwise indicated, conventional techniques from molecular biology (including recombinant techniques), cell biology, immunoassay technology, microscopy, image analysis, and analytical chemistry, which are within the skill of the art. Such conventional techniques include, but are not limited to, labeling of biological cells, immunostaining biological cells, detection of fluorescent signals, image analysis, selection of illumination sources and optical signal detection components, and the like. Such conventional techniques and descriptions can be found in standard laboratory manuals such as Robinson et al (Editors) Current Protocols in Cytometry (John Wiley & Sons, 2007); *Using Antibodies: A Laboratory Manual, Cells: A Laboratory Manual*, (both from Cold Spring Harbor Laboratory Press); Owens et al (Editors), Flow Cytometry Principles for Clinical Laboratory Practice: Quality Assurance for Quantitative Immunophenotyping (Wiley-Liss, 1994); Ormerod (Editor) Flow Cytometry: A Practical Approach (Oxford University Press, 2000); Coon, Diagnostic Flow Cytometry (Williams & Wilkins, 1991); Riley et al, Clinical Applications of Flow Cytometry (Igaku-Shoin Medical Publication, 1993); Stewart and Nicholson (Editors) Immunophenotyping (Wiley-Liss, 2000); Murphy, Fundamentals of Light Microscopy and Electronic Imaging (Wiley-Liss, 2001); Shapiro, Practical Flow Cytometry, Fourth Edition (Wiley-Liss, 2003); Herman et al, Fluorescence Microscopy, $2^{nd}$ Edition (Springer, 1998); all of which are herein incorporated in their entirety by reference for all purposes.

In one aspect, the invention provides a cell staining composition comprising a mixture of at least two labeled binding compounds one specific for CD45RA and one specific for a cell surface marker common to T-lymphocytes, preferably a T lymphocyte-specific marker, such as CD2 or CD3. The relative proportions of each binding compounds in the composition may vary widely and depend factors well-known to those with ordinary skill in the art, including the expected number of markers on each cell type, the specificity of the binding compounds for the markers, the stability of the marker-binding compound conjugates, the nature of the label employed, and the like. Labeled binding compounds used with the invention are readily available from commercial sources or by assembly using conventional techniques, such as disclosed in the above references. Preferably, binding compounds used in the invention are labeled with molecules that are capable of generating an optical signal. Preferably, the optical signal is a fluorescent signal generated by one or more fluorescent dye molecules attached to a binding compound.

A method of the invention may be implemented by, or include, the following steps: (a) combining under probe-binding conditions a blood sample with a first probe comprising at least a first binding compound specific for at least T-lymphocytes and a second binding compound distinct from the first binding compound, which second binding compound is specific for CD45RA molecules, wherein the first probe being capable of generating a first optical signal; (b) measuring the first optical signal generated by the first probe on cells in the sample; and (c) determining lymphocytes of sample by the values of the first optical signal from the first probe. In accordance with the method, lymphocytes will correspond to cell with high signal values. As used herein, "probe-binding conditions" means reaction conditions that enable, and preferably maximize, the specific binding of the binding compounds of a probe to their respective target molecules. Such conditions include both physical and chemical conditions, such as pH, salt, temperature, and the like. Chemical conditions may be controlled by use of buffers, e.g. phosphate buffer, and chelating agents, and the like. Preferably, binding compounds are monoclonal antibodies, so that conditions for maximizing specificity are well known to those in the art.

Probes of the invention are combined with a sample using conventional techniques. Usually, probes of the invention are combined under antibody-binding conditions in a reaction vessel, which may be a conventional test tube, a microtiter well, or the like, after which it is allowed to incubate for a sufficient time to permit stable complexes to formed between binding compounds and their respective target molecules, if present. Selecting volumes, buffer types and concentrations, and other reaction ingredients is well-known to those of ordinary skill, as exemplified in the above references. A sample analyzed by the invention may be any biological sample that contains lymphocytes, including, for example, whole blood, whole blood that has been processed to remove components, isolated white blood cells, lymphatic fluids, and the like. Preferably, the sample employed is whole blood; that is, blood removed from an organism, individual, patient, or the like, without processing or treatment prior to analysis. Guidance for making measurements on whole blood samples is provided in the following exemplary references that are incorporated by reference: U.S. Pat. Nos. 4,882,284; 5,627,037; 6,951,727 and 4,727,020.

In some embodiments of the invention where whole blood is being analyzed, an optional step may be included for removing or eliminating red blood cells from a sample in order to eliminate or reduce their interference in detecting white blood cells. In one embodiment, such elimination is accomplished by lysing red blood cells in the sample. The persistence of erythrocytes in the whole blood sample beyond the staining step may complicate later efforts to measure fluorophore bound specifically to the nucleated cells in the sample. Thus, in such circumstances the methods of the present invention may include, for example, after the antibody incubation step and before the flow cytometric acquisition of data, a further step of lysing the erythrocytes in the sample. A number of agents that serve simultaneously to lyse red blood cells and to fix nucleated cells in a whole blood sample, without interfering with binding of antibody to the nucleated cells, are known in the art. These agents are described, inter alia, in U.S. Pat. Nos. 4,654,312; 4,902,613; 5,510,267; 5,516,695; 5,648,225 and European Patent No. EP 161770 B1, the disclosures of which are incorporated herein by reference. Several such agents are available commercially, including FACS™ Lysing Solution (Becton Dickinson Immunocytometry Systems, San Jose, Calif., catalogue No. 349202) and Whole Blood Lysing Solution (Caltag Laboratories, Inc., Burlingame, Calif., catalogue no. GAS-10).

The minimum duration of incubation with lysis reagent depends upon whether, after lysis, debris may be removed by centrifugation.

Labels

Optical labels used with the invention may include direct or indirect attachment of fluorescent moieties, calorimetric moieties, chemiluminescent moieties, and the like, to binding compounds. Reviews of labeling methodology that provide guidance for selection and attachment of labels to binding compounds include Haugland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Hermanson, Bioconjugate Techniques (Academic Press, New York, 1996); and the like. Particular dyes applicable to the invention are disclosed in the following sample of references: Menchen et al, U.S. Pat. No. 5,188,934 (4,7-dichlorofluorscein dyes); Begot et al, U.S. Pat. No. 5,366,860 (spectrally resolvable rhodamine dyes); Lee et al, U.S. Pat. No. 5,847,162 (4,7-dichlororhodamine dyes); Khanna et al, U.S. Pat. No. 4,318,846 (ether-substituted fluorescein dyes); Lee et al, U.S. Pat. No. 5,800,996 (energy transfer dyes); Lee et al, U.S. Pat. No. 5,066,580 (xanthene dyes): Mathies et al, U.S. Pat. No. 5,688,648 (energy transfer dyes); and the like. Labeling can also be carried out with quantum dots, as disclosed in the following patents and patent publications, incorporated herein by reference: U.S. Pat. Nos. 6,322,901; 6,576,291; 6,423,551; 6,251,303; 6,319,426; 6,426,513; 6,444,143; 5,990,479; 6,207,392; 2002/0045045; 2003/0017264; and the like. As used herein, the term "fluorescent signal generating moiety" means a signaling means which conveys information through the fluorescent absorption and/or emission properties of one or more molecules. Such fluorescent properties include fluorescence intensity, fluorescence life time, emission spectrum characteristics, energy transfer, and the like. In one aspect, optical labels of the invention are fluorescent signal generating moieties.

Other fluorophores include, inter alia, Alexa Fluor® 350, Alexa Fluor® 532, Alexa Fluor® 546, Alexa Fluor® 568, Alexa Fluor® 594, Alexa Fluor® 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3.5, Cy5.5, and Cy7 (Amersham Biosciences, Piscataway, N.J. USA, and others).

Fluorescence resonsant energy transfer (FRET) tandem fluorophores may also be used, such as PerCP-Cy5.5, PE-Cy5, PE-Cy5.5, PE-Cy7, PE-Texas Red, and APC-Cy7; also, PE-Alexa dyes (610, 647, 680) and APC-Alexa dyes. PerCP is described in U.S. Pat. No. 4,876,190, which is incorporated by reference. Cyanine resonance energy transfer tandem fluorophores ("tandem fluorophores", "tandem dyes", "tricolor stains") have recently expanded the choices of fluorophore available for single-laser, multi-color flow cytometric analysis. PE-CY5 tandem staining proves particularly well-suited for three-color analysis: the R-PE moiety, excited by the 488 nm light of an argon ion laser, serves as an energy donor, and CY5, acting as an energy acceptor, fluoresces at 670 nm, readily distinguishable from the emission of FITC and PE. Cyanine fluorophores are described in U.S. Pat. Nos. 5,268,486; 4,337,063; 4,404,289; 4,405,711; and in Mujumdar et al., Bioconj. Chem. 4:105-111 (1993); Southwick et al., Cytometry 11:418-430 (1990); Ernst et al., Cytometry 10:3-10 (1989); and Mujumdar et al., Cytometry 10:11-19 (1989), and cyanine energy resonance transfer tandem fluorophores are described, inter alia, in U.S. Pat. No. 5,714,386 and in Waggoner et al., Ann. NY Acad. Sci. 677:185-193 (1993) and Lansdorp et al., Cytometry 12:723-30 (1991), the disclosures of which are incorporated herein by reference.

In some embodiments of the invention, two or more probes are employed, such that each probe is labeled with a distinct optical label, such as a distinct fluorescent dye. In one aspect, such distinct fluorescent dyes are spectrally resolvable. In one embodiment, at least two spectrally resolvable fluorescent dyes are employed, and in another embodiment at least three spectrally resolvable fluorescent dyes are employed.

Detection and Enumeration of Labeled Cells

After staining cells in a sample with probes of the invention, optical signals, especially fluorescent signals, may be measured by a variety of conventional instruments, particularly microscopes and flow cytometers. The determination of absolute or relative numbers of lymphocytes or a subset of lymphocytes in a sample may be accomplished by identifying a subset of data that forms a distinguishable cluster within the totality of data. Identification of distinct clusters in either univariate or multi-variate data is well-known to those of ordinary skill, particularly for data acquired from measurements using a flow cytometer, as exemplified by the following references that are incorporated by reference: Bagwell et al, J. Histochem. Cytochem., 27: 293-296 (1979); Young, J. Histochem. Cytochem., 25: 935-941 (1977); Cox et al, Cytometry, 9: 291-298 (1988); Roederer et al, Cytometry, 45: 3741 (2001); Roederer et al, Cytometry, 45: 47-55 (2001); and the like. Typically, enumeration of cell types using flow cytometers or automated microscopes includes setting gating parameters, e.g. upper and lower signal values of the one or more optical labels used, which are characteristic of the cell types of interest. The instrument then automatically tabulates cell types corresponding to the selected parameters.

Guidance for using a flow cytometer for implementing the methods of the invention is provided in the following references: Flow Cytometry: A Practical Approach, 2nd ed., M. G. Ormerod (ed.), Oxford University Press, 1997; Handbook of Flow Cytometry Methods, J. Paul Robinson (ed.), John Wiley & Sons (1993); Current Protocols in Cytometry, J. Paul Robinson (ed.), John Wiley & Sons (October 1997, with periodic updates); Becton Dickinson Cytometry Source Book, Becton Dickinson Immunocytometry Systems (1998, with periodic updates) (San Jose, Calif.), the disclosures of which are incorporated by reference.

Exemplary microscopes for slide-based analysis of samples include an iCyte™ Automated Imaging Cytometer (CompuCyte Corp., Cambridge, Mass.) (e.g. Kamensky et al, Cytometry, 12A: 381 (1991)); an Axioplan 2 MOT microscope (Carl Zeiss, Goettingen, Germany), e.g. equipped with 100 W Mercury lamp, 12 bit Axiocam CCD camera, and motorized object desk and filter changer; or like systems.

Kits for Practicing Methods of the Invention

In the commercialization of the methods described herein, certain kits for detection of specific cell types using probes of the invention will be particularly useful. Such a test kit typically comprises one or more reagents, such as, without limitation, probes comprising one or more labeled binding compounds, packaged in a container, such as, without limitation, a vial, tube or bottle, in a package suitable for commercial distribution, such as, without limitation, a box, a sealed pouch, a blister pack and a carton. In one aspect, kits are provided for identifying and counting lymphocytes in whole blood, which kits comprise a first probe comprising a first binding compound specific for CD45RA and a second binding compound specific for a cell surface marker common to T-lymphocytes, wherein preferably the first and second binding compounds have the same label. Preferably, the cell surface marker common to T lymphocytes is a T lymphocyte-specific marker, such as CD2 or CD3. Preferably, the first and second binding compounds are labeled with a fluorescent dye, such as a fluorescent dye selected from those listed above. In a particular embodiment of the invention, binding compounds are preferably labeled with a fluorescent dye selected from the group consisting of phycoerythrin (PE), peridinin chlorophyll protein-Cy5.5 (PerCP-Cy5.5), PE-Cy7, allophycocyanin (APC), Alexa Fluor 647, Cy5, APC-Cy5.5, APC-Cy7, or APC-Alexa Fluor 750. More preferably, such group consists of phycoerythrin (PE), peridinin chlorophyll protein-Cy5.5 (PerCP-Cy5.5), PE-Cy7, allophycocyanin (APC), APC-Cy5.5, or APC-Cy7.

In another aspect, kits of the invention are provided for determining the percentage of one or more types within a sample of white blood cells, for example, contained within a sample of whole blood. In one embodiment such kits comprise (i) a first probe as described above, (ii) a second probe comprising a binding compound specific for a monocyte-specific marker, such as CD14, wherein a portion of such binding compound is labeled with the same optical label as the first probe (a first optical label) and the remainder being labeled by a distinct optical label (a second optical label), and (iii) a third probe comprising a binding compound specific for a granulocyte-specific marker, such as CD15, wherein such binding compound is labeled with the second optical label. In another embodiment, the binding compounds of the second probe are labeled with an optical label (a third optical label) distinct from the first and second optical labels. This latter embodiment may be useful to better distinguish the three populations of white blood cells, e.g. as may be necessary for some choices of detection methods, optical labels, binding compounds, and the like. In one embodiment, the first, second, and/or third optical labels are fluorescent labels. For the former kit of this aspect of the invention, preferably a first optical label is PerCP and a second optical label is APC. In the latter kit of this aspect, preferably a first optical label is PerCP, a second optical label is APC, and a third optical label is PE-Cy5.5. In other embodiments, such optical labels may be interchanged among the respective binding compounds for additional forms of the compositions and kits of the invention.

The constituents of the kits may be packaged together or separately, and each constituent may be presented in one or more tubes or vials, or in cartridge form, as is appropriate. The constituents, independently or together, may be packaged in any useful state, including without limitation, in a dehydrated, lyophilized, classified or aqueous state. In a preferred embodiment, kits of the invention are in the form of a disposable cartridge having probes incorporated in appropriate reaction chambers as dried reagents. In particular, such dried reagents may be incorporated as films and/or coatings within such cartridge.

EXAMPLES

Several examples of the probes of the invention were prepared and tested on whole blood samples from normal individuals. Commercially available reagents (e.g. BD Biosciences, San Jose, Calif.) were employed and used in accordance with manufacturer's instructions. Unless otherwise noted, scatter and fluorescent intensity measurements were made on a FACSCanto flow cytometer (BD Biosciences, San Jose, Calif.).

Figure 1A:
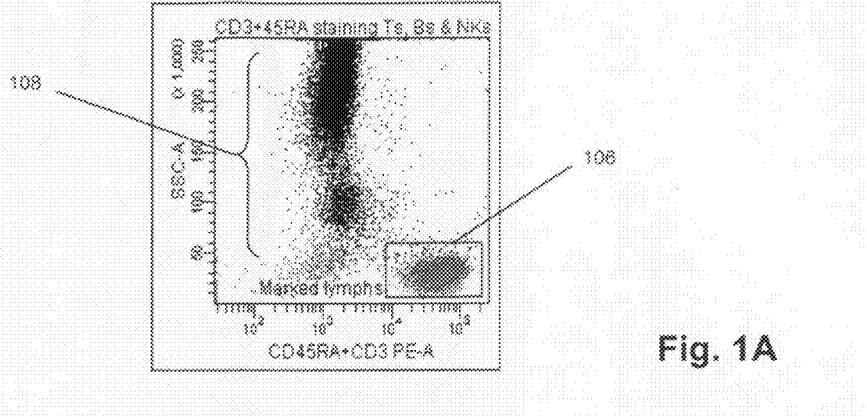
FIG. 1A shows a scatter plot of side-light scatter intensities and fluorescence intensities of white blood cells labeled with a probe comprising two antibodies, one with specificity for CD45RA and one specificity for CD3. Both antibodies are labeled with phycoerythrin (PE) and measurements were made with a flow cytometer.
Figure 1B:
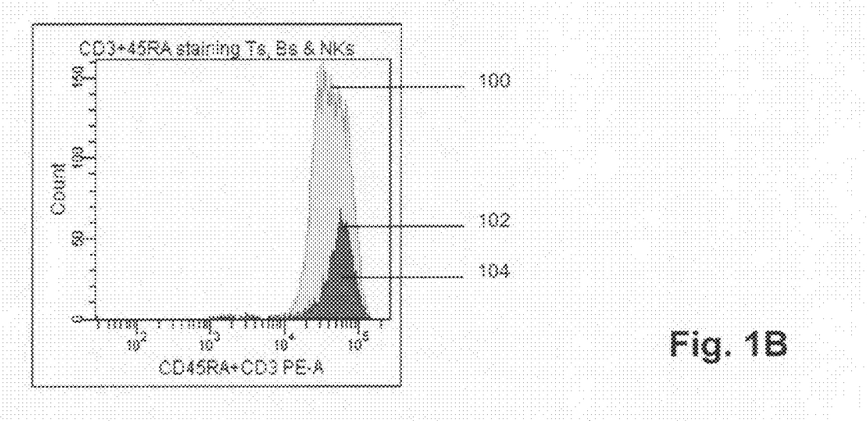
FIG. 1B shows a histogram of counts versus signal intensity for only the lymphocytes of FIG. 1A, wherein the peaks of the overlapping histograms correspond to the identification lines connecting the peaks to their respective identification numbers, 100, 102 and 104.
Figure 1C:
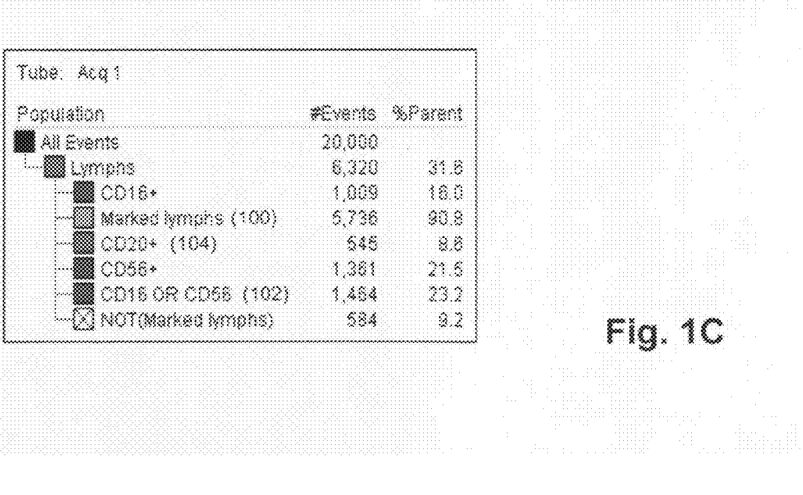
FIG. 1C contains a tabulation count data corresponding to the plots of FIGS. 1A and 1B.

50 µL whole blood was combined with 20 µL anti-CD45RA antibody labeled with phycoerythrin (PE) (BD Biosciences, San Jose, Calif.), 20 µL anti-CD3 antibody labeled with phycoerythrin (PE) (BD Biosciences, San Jose, Calif.), 5 µL anti-CD16 antibody labeled with PE-Cy7 (BD Biosciences, San Jose, Calif.), 5 µL anti-CD56 antibody labeled with APC (BD Biosciences, San Jose, Calif.), and 20 µL anti-CD20 antibody labeled with PerCP-Cy5.5 (BD Biosciences, San Jose, Calif.), after which side scatter and PE fluorescence measurements were made with a FACSCanto flow cytometer. Portions of the resulting data from the measurements are shown in FIG. 1A. Box (106) indicates a cluster corresponding to lymphocytes. FIG. 1B displays data from lymphocytes in counts versus PE fluorescence histogram in which total lymphocytes (100) subpopulations of lymphocytes (102 for CD16+ or CD56+, and 104 for CD20+) are indicated. Low PE-fluorescence high scatter cells (108) correspond to non-lymphocyte white blood components, such as granulocytes and monocytes. FIG. 1C is a table giving count data corresponding to FIGS. 1A and 1B.

Figure 2A:
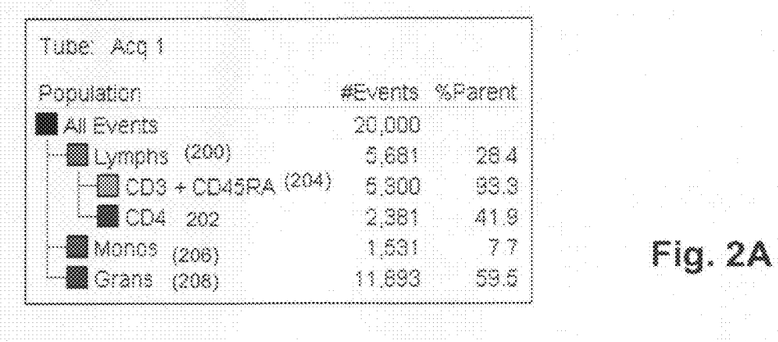
FIG. 2A contains a tabulation of count data shown in the plot of FIG. 2B.
Figure 2B:
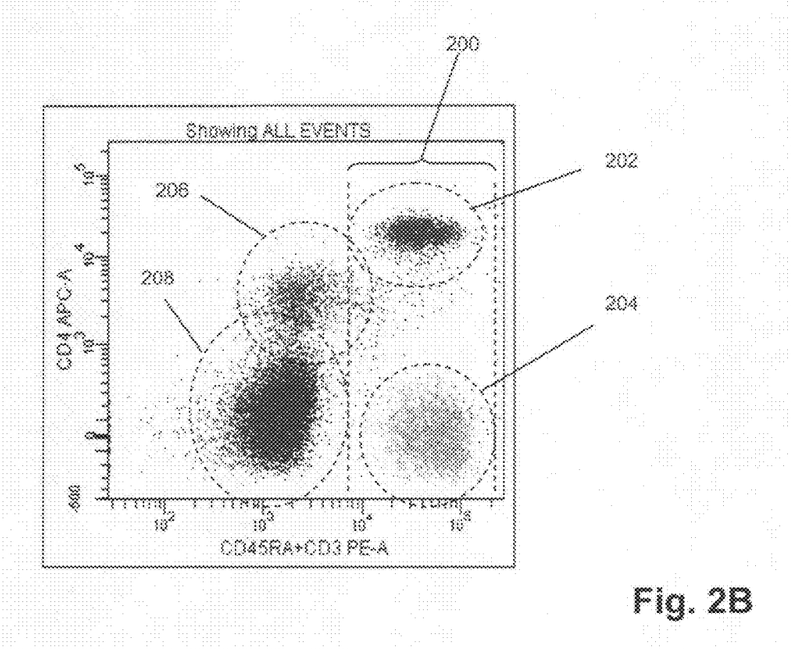
FIG. 2B shows a two-dimensional scatter plot of fluorescent intensities of white blood cells labeled with first and second probes, the first probe being specific for CD4 and being labeled with APC, and the second probe comprising two antibodies one specific for CD45RA and one specific for CD3 and both antibodies being labeled with PE. Measurements were made with a flow cytometer.

In another experiment, 50 µL whole blood was combined with 20 µL anti-CD45RA antibody labeled with phycoerythrin (PE) (BD Biosciences, San Jose, Calif.), 20 µL anti-CD3 antibody labeled with phycoerythrin (PE) (BD Biosciences, San Jose, Calif.), 5 µL anti-CD4 antibody labeled with APC (BD Biosciences, San Jose, Calif.), after which APC and PE fluorescence measurements were made with a FACSCanto flow cytometer. As shown in FIG. 2B, clearly distinguishable clusters of fluorescence data corresponding to lymphocytes or their subset are produced. Lymphocytes correspond to high PE fluorescence in region (200) that is distinguishable from cells with low PE fluorescence values (e.g. clusters 206 and 208). Among lymphocytes (200), CD4+ lymphocytes are shown in high-PE high-APC fluorescence cluster (202), whereas non-CD4+ lymphocytes are shown in a clearly distinguishable high-PE low-APC fluorescence cluster (204). Separate clusters of high APC low PE fluorescence (206) and low APC low PE fluorescence (208) correspond to monocytes and granulocytes, respectively.

Figure 3A:
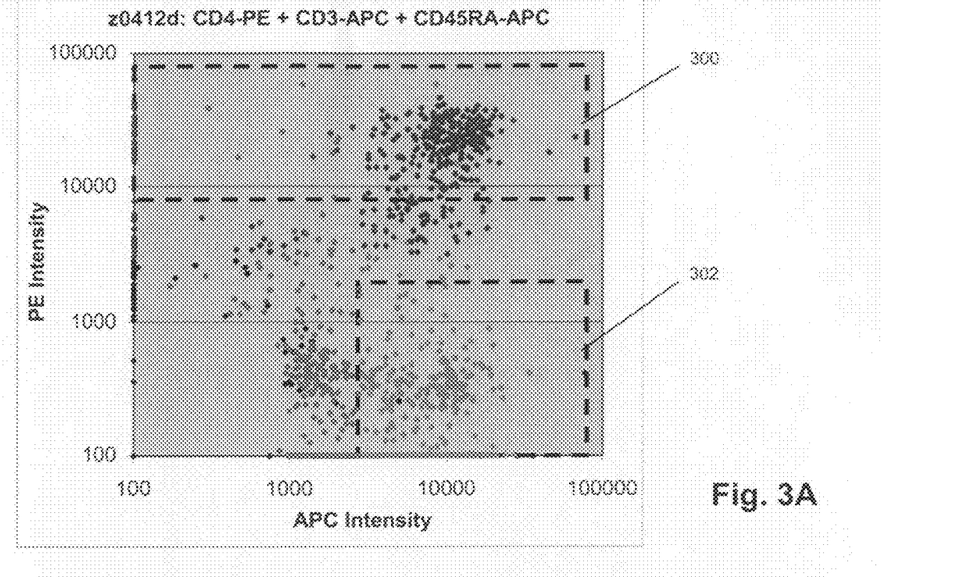
FIG. 3A shows a two-dimensional scatter plot of fluorescent intensities of white blood cells labeled with first and second probes, the first probe being specific for CD4 and being labeled with PE, and the second probe comprising two antibodies one specific for CD45RA and one specific for CD3 and both antibodies being labeled with APC. Measurements were made with a low magnification imaging microscope.
Figure 3B:
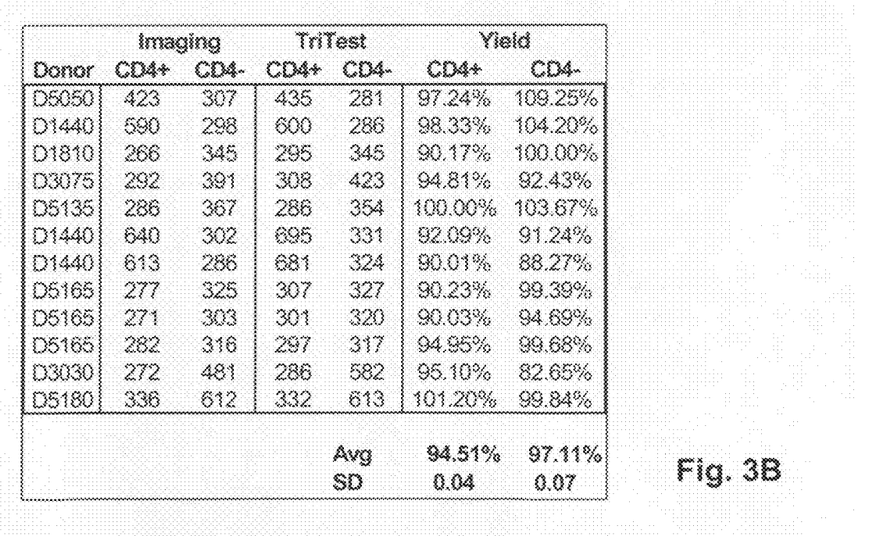
FIG. 3B contains a tabulation of the data shown in FIG. 3A as well as comparative data from a commercially available assay (TriTest) for CD4+ cells.

In another experiment, 50 µL whole blood was combined with 20 µL anti-CD45RA antibody labeled with APC (BD Biosciences, San Jose, Calif.), 20 µL anti-CD3 antibody labeled with APC (BD Biosciences, San Jose, Calif.), 5 µL anti-CD4 antibody labeled with PE (BD Biosciences, San Jose, Calif.), after which APC and PE fluorescence measurements were made with a low magnification imaging microscope. Image data was collected from stained cells disposed on a slide with a CCD camera. Image data for both PE fluorescence and APC fluorescence were collected so that PE and APC intensity values were collected for each cell in a defined field of the slide. A scatter plot of such data is shown in FIG. 3A, where data cluster in region (300) corresponds to CD4+ lymphocytes and data cluster in region (302) corresponds to non-CD4+ lymphocytes. FIG. 3B is a tabulation of counts of the indicated cell types based on the imaging measurements and counts using a commercially available staining assay (TriTest, BD Biosciences, San Jose, Calif.) with fluorescence measurements using a flow cytometer.

FIG. 4 contains scatter plots of side scatter and fluorescence measurements made using the probe of the invention. In this example, the probe of the invention was formed by combining an anti-CD45RA antibody labeled with FITC and components of a commercially available kit (TriTest CD3/4/45) that contains anti-CD3, anti-CD4, and anti-CD45 antibodies labeled with PE. Panels of several scatter plots are shown that correspond to measurements with and without the anti-CD45RA component. 50 µL whole blood was combined with 20 µL staining cocktail (TriTest alone) or 25 µL staining cocktail (TriTest reagent plus CD45RA stain), and incubated for 15 minutes at room temperature in the dark, after which 450 µL of red blood cell lysing agent (FACSLyse, BD Biosciences, San Jose, Calif.) was added. After a further 15 minutes incubation, the resulting sample was analyzed direction using a FACSCalibur flow cytometer. As with the above examples, the panel in the lower rightmost position shows that clusters of lymphocytes are clearly distinguishable from other cells and that the cluster of CD4+ lymphocytes is clearly distinguishable from non-CD4+ lymphocytes.

DEFINITIONS

Generally, terms used herein not otherwise specifically defined have meanings corresponding to their conventional usage in the fields related to the invention, including analytical chemistry, biochemistry, molecular biology, cell biology, microscopy, image analysis, and the like, such as represented in the following treatises: Alberts et al, Molecular Biology of the Cell, Fourth Edition (Garland, 2002); Nelson and Cox, Lehninger Principles of Biochemistry, Fourth Edition (W.H. Freeman, 2004); Murphy, Fundamentals of Light Microscopy and Electronic Imaging (Wiley-Liss, 2001); Shapiro, Practical Flow Cytometry, Fourth Edition (Wiley-Liss, 2003); Owens et al (Editors), Flow Cytometry Principles for Clinical Laboratory Practice: Quality Assurance for Quantitative Immunophenotyping (Wiley-Liss, 1994); Ormerod (Editor) Flow Cytometry: A Practical Approach (Oxford University Press, 2000); and the like.

"Antibody" or "immunoglobulin" means a protein, either natural or synthetically produced by recombinant or chemical means, that is capable of specifically binding to a particular antigen or antigenic determinant. Antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a. constant domain at its other end; the constant domain of the light chain is aligned with the first constant domain of the heavy chain, and the light chain variable domain is aligned with the variable domain of the heavy chain. The constant domains are not involved directly in binding an antibody to an antigen. Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. "Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, the monoclonal antibodies are advantageous in that they can be synthesized by hybridoma culture, uncontaminated by other immunoglobulins. Guidance in the production and selection of antibodies for use in immunoassays can be found in readily available texts and manuals, e.g. Harlow and Lane, Antibodies: A Laboratory Manual (Cold Spring Harbor Laboratory Press, New York, 1988); Howard and Bethell, Basic Methods in Antibody Production and Characterization (CRC Press, 2001); Wild, editor, The Immunoassay Handbook (Stockton Press, New York, 1994), and the like.

"Antigenic determinant," or "epitope" means a site on the surface of a molecule, usually a protein, to which a single antibody molecule binds; generally a protein has several or many different antigenic determinants and reacts with antibodies of many different specificities. A preferred antigenic determinant is a phosphorylation site of a protein.

"Binding compound" means a compound that is capable of specifically binding to a particular target molecule. Examples of binding compounds include antibodies, lectins, nucleic acids, aptamers, and the like, e.g. Sharon and Lis, Lectins, $2^{nd}$ Edition (Springer, 2006); Klussmann, The Aptamer Handbook: Functional Oligonucleotides and Their Applications (John Wiley & Sons, New York, 2006). Preferably, binding compounds are antibodies, and more preferably, binding compounds are monoclonal antibodies.

"CD2" means a cell surface molecule of the cluster designation (CD) system, also known as T11 or LFA-2, that is expressed on T cells, thymocytes, and NK cells, and that functions as an adhesion molecule, binding CD58 (LFA-3). Preferably, CD2 refers to the human CD2 molecule.

"CD3" means a cell surface molecule of the cluster designation (CD) system, also known as T3, that is expressed on T cells and thymocytes, and that is associated with the T cell antigen receptor (TCR), is required for cell surface expression of and signal transduction by TCR. Its cytoplasmic domains contain ITAM motifs and bind cytoplasmic tyrosine kinases. Preferably, CD3 refers to the human CD3 molecule.

"CD4" means a cell surface molecule of the cluster designation (CD) system, also known as T4 or L3T4, that is expressed on thymocyte subsets, helper and inflammatory T cells (about two thirds of peripheral T cells), monocytes, macrophages, and that functions as coreceptor for MHC class II molecules, binds Lck on cytoplasmic face of membrane. CD4 is a receptor for HIV-I and HIV-2 gp120. Preferably, CD4 refers to the human CD4 molecule.

"CD45RA" means a cell surface molecule of the cluster designation (CD) system that is expressed on B cells, T cell subsets (naive T cells), and monocytes, and that is a splice variant of CD45 containing the A exon. Preferably, CD45RA refers to the human CD45RA molecule.

"CD56" means a cell surface molecule of the cluster designation (CD) system, also known as NKH-1, that is expressed on NK cells, and that is a splice variant of the Neural Cell Adhesion Molecule (NCAM). Preferably, CD56 refers to the human CD56 molecule.

"Complex" as used herein means an assemblage or aggregate of molecules in direct or indirect contact with one another. In one aspect, "contact," or more particularly, "direct contact" in reference to a complex of molecules, or in reference to specificity or specific binding, means two or more molecules are close enough so that attractive noncovalent interactions, such as Van der Waal forces, hydrogen bonding, ionic and hydrophobic interactions, and the like, dominate the interaction of the molecules. In such an aspect, a complex of molecules is stable in that under assay conditions the complex is thermodynamically more favorable than a non-aggregated, or non-complexed, state of its component molecules. As used herein, "complex" usually refers to a stable aggregate of two or more proteins. In one aspect, a "complex" refers to a stable aggregate of two proteins, such as an antibody specifically bound to an antigenic determinant of a target protein.

"Dried reagents" mean assay reagents, such as buffers, salts, active compounds, such as enzymes, co-factors, and the like, or binding compounds, such as antibodies, aptamers, or the like, that are provided in a dehydrated formulation for the purpose of improved shelf-life, ease of transport and handling, improved storage, and the like. The nature, composition, and method of producing dried reagents vary widely and the formulation and production of such materials is well-known to those of ordinary skill in the art as evidenced by the following references that are incorporated by reference: Franks et al, U.S. Pat. No. 5,098,893; Cole, U.S. Pat. No. 5,102,788; Shen et al, U.S. Pat. No. 5,556,771; Treml et al, U.S. Pat. No. 5,763,157; De Rosier et al, U.S. Pat. No. 6,294, 365; Buhl et al, U.S. Pat. No. 5,413,732; McMillan, U.S. patent publication 2006/0068398; McMillan et al, U.S. patent publication 2006/0068399; Schwegman et la (2005), Pharm. Dev. Technol., 10: 151-173; Nail et al (2002), Pharm. Biotechnol., 14: 281-360; and the like. Dried reagents include, but are not limited to, solid and/or semi-solid particulates, powders, tablets, crystals, films, coatings, and the like, that are manufactured in a variety of ways. In one aspect, dried reagents are lyophilized coatings or films on the inner walls of vessels or inside a chamber of a disposable cartridge for carrying out an assay in accordance with the invention. Dried reagents may include excipients, which are usually inert substances added to a material in order to confer a suitable consistency or form to the material. A large number of excipients are known to those of skill in the art and can comprise a number of different chemical structures. Examples of excipients, which may be used in the present invention, include carbohydrates, such as sucrose, glucose, trehalose, melezitose, dextran, and mannitol; proteins such as BSA, gelatin, and collagen; and polymers such as PEG and polyvinyl pyrrolidone (PVP). The total amount of excipient in the lyophilized particulate may comprise either single or multiple compounds. In some embodiments, the type of excipient is a factor in controlling the amount of hygroscopy of a dried reagent. Lowering hygroscopy can enhance the a dried reagent's integrity and cryoprotectant abilities. However, removing all water from such a composition would have deleterious effects on those reaction components, proteins for example, that require certain amounts of bound water in order to maintain proper conformations.

"Granulocyte-specific marker" means any molecule that is present on or in substantially all granulocytes, but is substantially absent from other white blood cell types. Exemplary granulocytes-specific markers include, but are not limited to, the following molecules: 1C3, 3C4, 6D10, 2B2, 8C5, alkaline phosphatase, calprotectin, CD18, CD15, CD16, CD24, CD32, CD34, CD45, CD66b, CEACAM8, DH59B, EMR3, eosinophil cationic protein, granulocyte factor, GMP, Gr-1 (Ly-G6), granulocyte elastase, HIS48, IL-8, leukocyte alkaline phosphatase, LRG, myeloperoxidase, NKH1, and the like. Preferably, granulocytes-specific markers are cell surface molecules. More preferably, granulocytes-specific markers are the human equivalent of the markers listed above. Still more preferably, a granulocytes-specific marker is CD15.

"Kit" means to any delivery system for delivering materials or reagents for carrying out a method of the invention. In the context of assays for analyzing white blood cells, such delivery systems include systems that allow for the storage, transport, or delivery of assay reagents (e.g., probes, ancillary labeling antibodies, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain buffers and a reaction cuvette, vessel, or the like, for use in an assay, while a second container may contain probes. Optional additional components may include, sample-extraction apparatus, e.g. skin puncturing devices for exposing small amounts of blood, germicidal swabs, or the like.

"Monocyte-specific marker" means any molecule that is present on or in substantially all monocytes, but is substantially absent from other white blood cell types. Exemplary monocyte-specific markers include, but are not limited to, the following molecules: 125I-WVH-1, 63D3, CB12, CD11a, CD14, CD15, CD54, CD62L, CD163, cytidine deaminase, DH59B, Fc-receptors, Flt-1, hMGL, Ki-M1p, Leu-7, lysozyme, leucocyte tartrate-resistant acid phosphatase, mannosyl receptors, peanut agglutinin, thromboplastin, thymidine phosphorylase, TNF, urokinase, and the like. Preferably, monocytes-specific markers are cell surface molecules. More preferably, monocytes-specific markers are the human equivalent of the markers listed above. Still more preferably, a monocytes-specific marker is CD14.

"Sample" means a quantity of material from a biological, environmental, medical, or patient source in which detection or measurement of target cells, particles, beads, and/or analytes is sought. The term "sample" encompasses biological samples, e.g. a quantity of blood, a microbiological culture, or the like; environmental samples, e.g. a soil or water sample; medical samples or specimens, e.g. a quantity of blood or tissue; or the like. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention. The terms "sample" and "specimen" are used interchangeably.

"Specific" or "specificity" in reference to the binding of one molecule to another molecule means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least thirty percent. Generally, molecules involved in a specific binding event have areas on their surfaces, and/or in the case of proteins in cavities, giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

"Spectrally resolvable" in reference to a plurality of fluorescent labels, or dyes, means that the fluorescent emission bands of the dyes are sufficiently distinct, e.g. non-overlapping, that binding compounds to which the respective dyes are attached can be distinguished on the basis of the fluorescent signal generated by the respective dyes by conventional photodetection systems, e.g. employing a standard system of filters, mirrors, dichoics, photomultiplier tubes, photodiodes, or the like, such as described in the following, or like, references: Wheeless et al, Flow Cytometry: Instrumentation and Data Analysis (Academic Press, New York, 1985); Shapiro (cited above).

"T lymphocyte-specific marker" means any molecule that is present on or in substantially all T lymphocytes, but is substantially absent from other white blood cell types. Exemplary T lymphocyte-specific markers include, but are not limited to, the following molecules: CD1a, CD1d, CD2, CD3, CD4, CD5, CD7, CD8, CD25, CD38, CD45R0, CD72, CD134, CD150, CRTAM, FOXP3, FT2, GPCA, HML-1, HT23A, Leu-22, Ly-2, Ly-m22, MICG, MRC OX-8, MRC OX-22, OX40, PD-1, RT6, TCR, Thy-1 (CD90), TSA-2, and the like. Preferably, T lymphocyte-specific markers are cell surface molecules. More preferably, T lymphocyte-specific markers are the human equivalent of the markers listed above. Still more preferably, T lymphocyte-specific markers are CD2 or CD3 molecules.

The above teachings are intended to illustrate the invention and do not by their details limit the scope of the claims of the invention. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

What is claimed is:

1. A method for enumerating lymphocytes in a blood sample, the method comprising the steps of:
    combining said sample with a fluorescent dye-labeled first binding compound specific for a T lymphocyte-specific marker that is CD2 or CD3 and a fluorescent dye-labeled second binding compound specific for CD45RA, wherein said first binding compound and said second binding compound are labeled with the same fluorescent dye;
    measuring fluorescence signals from said fluorescent dye-labeled binding compounds that have bound to cells in said sample; and
    enumerating lymphocytes in said sample.

2. The method of claim 1 wherein said first and second binding compounds are antibodies.

3. A method for determining the percentage of CD4+ lymphocytes in a blood sample, the method comprising the steps of:
    combining said sample with a fluorescent dye-labeled first binding compound specific for a T lymphocyte-specific marker that is CD2 or CD3 and a fluorescent dye-labeled second binding compound specific for CD45RA, wherein said first binding compound and said second binding compound are labeled with a first fluorescent dye, and fluorescent dye-labeled third binding compound specific for CD4, wherein said third binding compound is labeled with a fluorescent dye that is distinct from said first fluorescent dye;
    measuring fluorescence signals from said fluorescent dye-labeled binding compounds that have bound to cells in said sample;
    enumerating lymphocytes in said sample;
    enumerating CD4+ lymphocytes in said sample; and
    determining the percentage of CD4+ lymphocytes in said sample.

4. The method of claim 3 wherein said first, second, and third binding compounds are antibodies.

* * * * *